United States Patent [19]

Bryden

[11] 4,058,810

[45] Nov. 15, 1977

[54] STABILIZED DIGITAL PPI RADAR SYSTEM

[75] Inventor: Joseph E. Bryden, Framingham, Mass.

[73] Assignee: Raytheon Company, Lexington, Mass.

[21] Appl. No.: 714,051

[22] Filed: Aug. 13, 1976

[51] Int. Cl.² .............................................. G01S 7/28
[52] U.S. Cl. ............................ 343/17.1 R; 343/17.7
[58] Field of Search .......................... 343/17.1 R, 17.7

[56] References Cited
U.S. PATENT DOCUMENTS

| 3,780,370 | 12/1973 | Reeves | 343/17.7 |
| 3,918,054 | 11/1975 | Collins | 343/17.1 R X |

Primary Examiner—T.H. Tubbesing
Attorney, Agent, or Firm—Herbert W. Arnold; Joseph D. Pannone; Milton D. Bartlett

[57] ABSTRACT

A radar system having the radar pulse rate controlled directly from an indicator unit. Separate modulator-transmitter-receiver and digital video processor indicator units are provided. A radar trigger pulse is produced by the processor unit in synchronism with the processor clock at a rate determined by the radar range setting. An acknowledge signal is produced in turn by the modulator-transmitter-receiver in accordance with an activating signal in the modulator and fed back to the indicator unit to start video signal digitization and the CRT sweep. Jitter between the start of the radar return signal and the radar sweep are eliminated.

8 Claims, 4 Drawing Figures

RADAR SYSTEM, 100

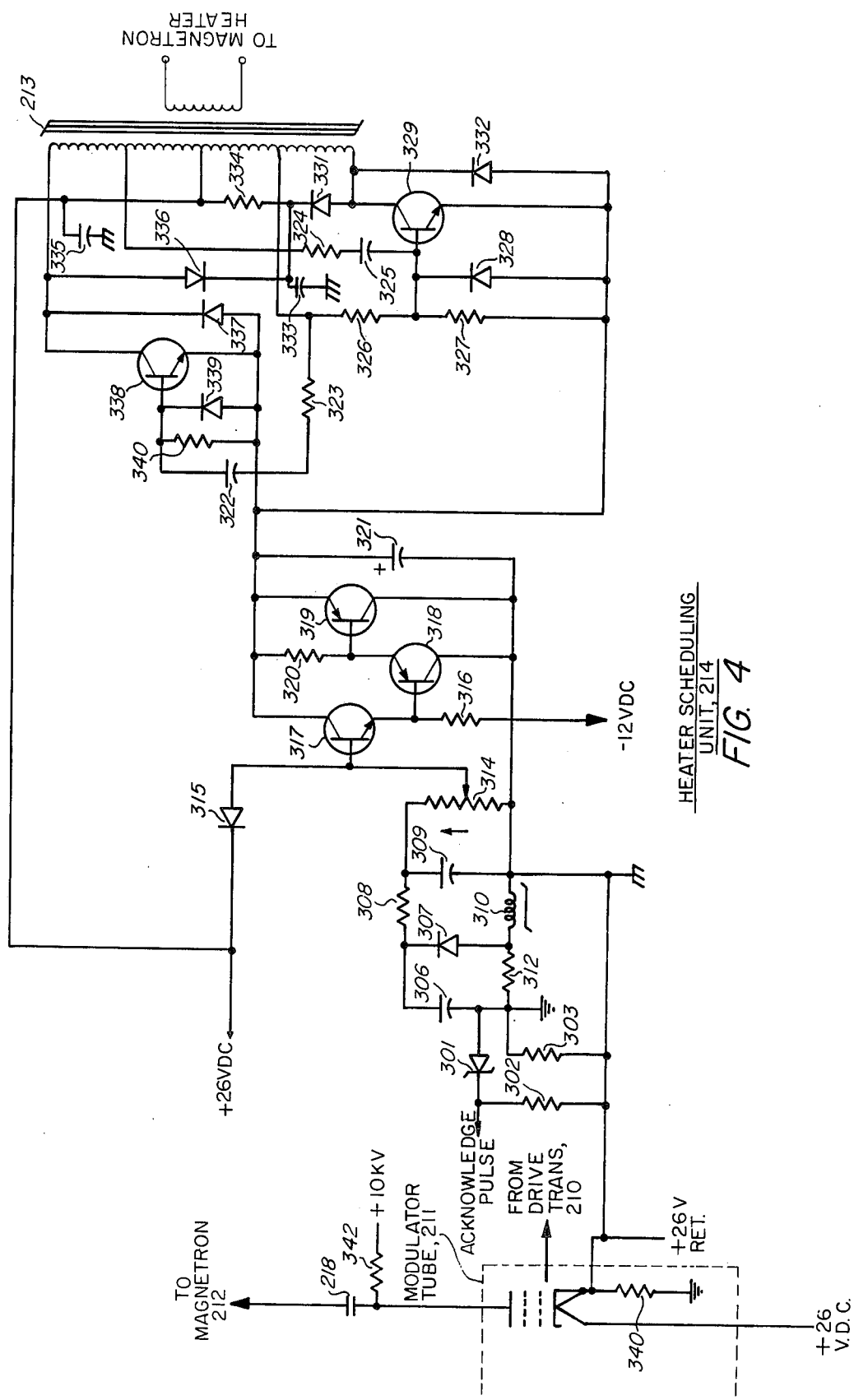
FIG. 4 HEATER SCHEDULING UNIT, 214

STABILIZED DIGITAL PPI RADAR SYSTEM

BACKGROUND OF THE INVENTION

1. Field of the Invention

The invention pertains to a radar system having a stabilized display presentation. The invention is particularly useful in marine radar systems having digitized video signals with processing thereof.

2. Description of the Prior Art

Marine radar systems of the prior art have generally operated in the PPI mode using pulsed operation. The repetition rate of the pulses, termed the PRF (pulse repetition frequency), was determined in accordance with an internal oscillator. One PRF triggering pulse was produced for each radar return time or radial scan line.

In the display presentation of the returned radar signals, the sweep starting out from the radar center was commenced by the same PRF triggering pulse or at a fixed time delay thereafter. Unfortunately, a problem arose in that the actual time elapsed between the commencement of the PRF triggering pulse and the emission of a pulse from the radar antenna was subject to variation by a number of factors. As the range of display was changed, the pulse width and average power from the transmitter ouput stage also changed causing the final output tube to fire at different times after the commencement of the PRF pulse depending upon the range chosen by the operator. The problem has been found to be particularly acute when solid state modulators are used. Also, aging of the final output tube or other components in the tramsmitting circuitry caused unwanted variations. Variations could appear between adjacent pulse times as well as between complete sweeps or between ranges.

Because of these variations, an uneven display of received signals was made. The target would tend to appear jagged or be presented out of position upon succeeding sweeps. The jagged edge problem was particularly apparent if digital processing of received signals was employed.

Accordingly, it is object of the present invention to provide a radar system in which the display of received signals is stabilized and synchronized to the actual transmission of radar pulses.

It is also an object of the present invention to provide such a system having a stabilized presentation and further employing digital processing of received radar signals.

SUMMARY OF THE INVENTION

These, as well as other objects of the invention, may be met by providing the combination of means for initiating the production of radar pulses and means for producing a signal having a predetermined time relationship, such as a fixed delay time, to the radar pulses. Means is provided for producing the radar pulses in response to the initiating means. The radar pulse producing means further includes a modulating stage and a transmitting stage. The radar pulse production initiating means operates in response to the modulating means such as by sensing a control or signal current or voltage therein. The modulating stage means may be either a tube modulator or a solid state modulator. In the case of a tube modulator, a hard-tube is preferred.

The invention may also be practiced by a radar system which comprises the combination of means for initiating the production of radar pulses, means for transmitting the radar pulses in response to the initiating means, means for producing a signal having a predetermined time relationship such as a fixed delay time to the radar pulses, means for receiving the radar return signals, and means for producing a visual display in response to the received return radar signals, and means for synchronizing operations of the display producing means in response to the signal which has a predetermined time relationship to the radar pulses. The combination may further include means for producing representations such as digital representations of the received radar return signals, means for storing at least some of the representations, means for writing the representation into the storing means at a first rate, and means for reading the representations out of the storing means at a second rate. Operations of the writing means and the reading means are synchronized by the signal having a predetermined time relationship to the radar pulses. In preferred embodiments, the commencement of operation of the writing and reading means is controlled by the time of commencement of the signal. The second rate in a preferred embodiment is less than the first rate for at least some ranges of a radar range setting and may be constant for or among at least some of the ranges of the radar range setting. The radar preferably operates in the PPI mode of operation. The storing means in the preferred embodiments stores the representations for a single radar pulse period before they are read out again. Preferably, the representations are digital samples of returned radar signals although analog samples may be used as well.

Objects of the invention may also be met by a radar system comprising the combination of means for initiating the production of radar pulses, means for transmitting the pulses, means for actuating the transmitting means in response to the initiating means, means for producing a signal having a predetermined time relationship to the radar pulses in which the signal producing means operates in response to the actuating means, means for receiving the return radar signals, and means for producing a display in response to the received returned radar signals. The means for producing the signal having a predetermined time relationship to the radar pulses preferably comprises means for sensing one or more signals of or within the initiating means circuitry. The initiating means may comprise a modulator tube with means for sensing the cathode current in the tube. A solid state modulator may also be used. For the transmitting means, a magnetron tube is preferred. The repetition rate of the pulses may be varied as may be their width.

BRIEF DESCRIPTION OF THE DRAWINGS

FIG. 4 is a schematic diagram of the heater scheduling circuit shown in FIG. 3.

DESCRIPTION OF THE PREFERRED EMBODIMENTS

Figure 1:
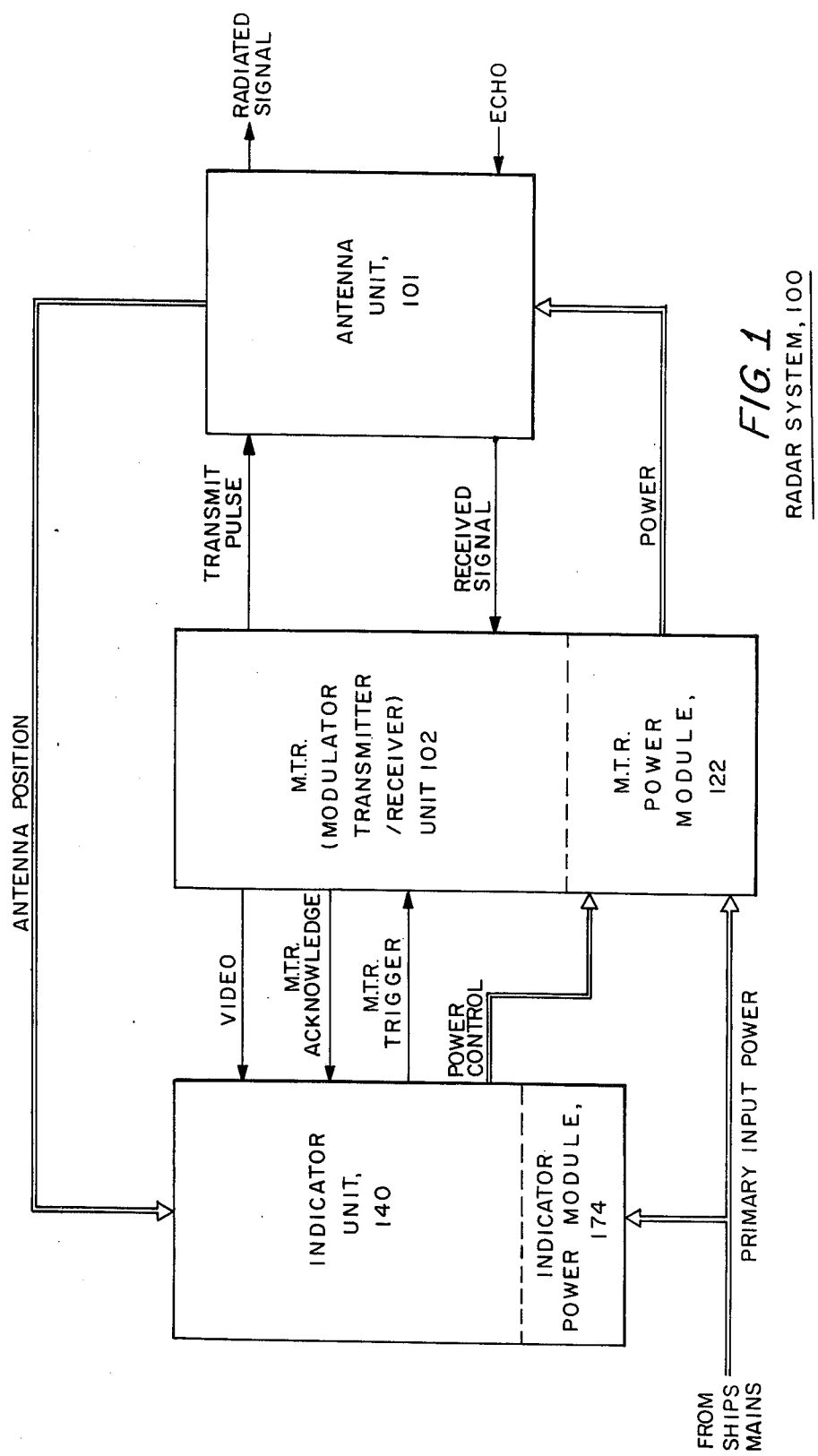
FIG. 1 is a basic block diagram of a radar system of the invention.

Referring first to FIG. 1, there is shown a basic block diagram of a PPI radar system 100 constructed in accordance with the teachings of the present invention. The radar system is constructed from three basic units: indicator unit 140, MTR (modulator-transmitter-receiver) unit 102, and antenna unit 101. Indicator unit 140, which provides the display of radar information and contains the operating controls of the system, is ordinarily mounted upon the bridge of the ship for easy access and convenience for use in navigation. Antenna unit 101 is in practice mounted as high as possible with an unobstructed path for the antenna beam to maximize the range of the unit. MTR unit 102 is located in weather-tight position as close as is practical to antenna unit 101 to minimize losses in the high-power transmit pulses coupled to antenna unit 101 and the low-level receive signals coupled from antenna unit 101 to MTR unit 102.

Both indicator unit 140 and MTR unit 102 contain separate power modules 174 and 122 respectively. Both take the ship's power which may be 110 volts AC 60 cycles or any other normally provided primary input power source and convert it to DC voltages suitable for operating the various electronic circuits and electromechanical devices located within the two units. Additionally, MTR power module 122 supplies operating power to antenna 101 to the motor contained therein for rotation of the antenna. By providing separate power modules in each of the two remotely located major operating units, losses which occurred in previous units in the cabling between units is avoided. Moreover, with the system of the present invention, ON/OFF control of MTR power module 122 is accomplished from indicator unit 140 using only low signal level control voltages. Full control is therefore maintained at the indicator unit without large amounts of power dissipation and loss in long runs of cabling between units.

Each radar pulse cycle is initiated at indicator unit 140 by the production of a MTR TRIGGER pulse which is coupled to MTR unit 102. Upon receipt of this pulse, MTR unit 102 produces a high-power transmit pulse. The transmit pulse is coupled to antenna unit 101 which radiates the signal outward in a narrow beam. Echo return signals from targets are received at antenna unit 101 and relayed to the receiver portion of MTR unit 102. The receiver portion of MTR unit 102 amplifies and detects the received echo signals and produces a video signal to indicator unit 140. The commencement of the video signal is marked by an acknowledge pulse generated within MTR unit 102. Indicator unit 140 produces a visual display of the signals reflected back from targets in the path of the radar beam in accordance with the video signal. The azimuthal position of the radar antenna is relayed from antenna unit 101 directly to antenna unit 140 to indicate the angle upon the display screen the returned radar signals are to be displayed.

Figure 2:
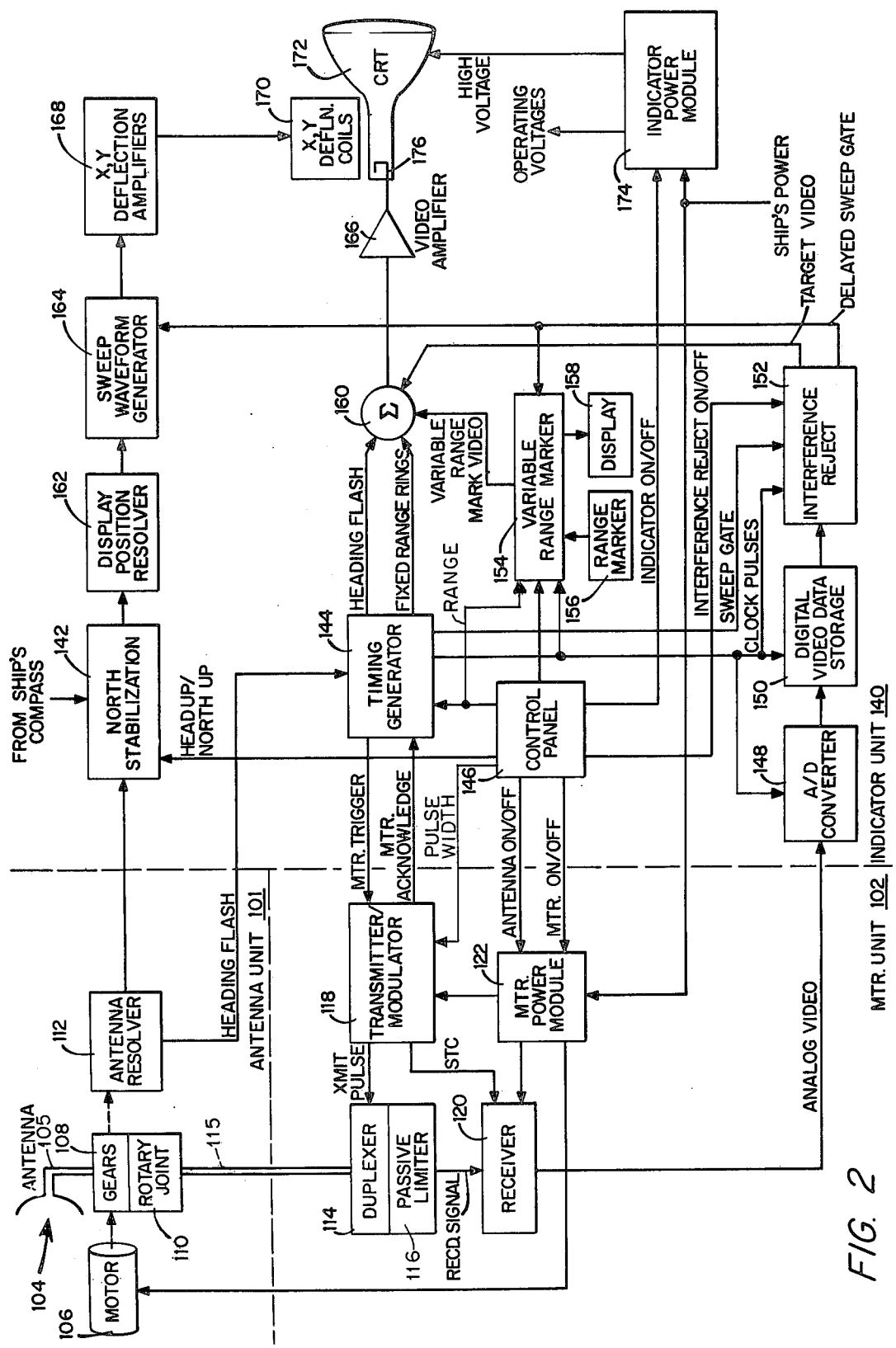
FIG. 2 is a detailed block diagram of a radar system of the invention.

Referring next to FIG. 2, there is shown a detailed block diagram of radar system 100 as shown in FIG. 1. Antenna unit 101 contains a rotatable antenna 104 capable of radiating and receiving signals within the frequency range of the radar pulses. Antenna 104 is rotatably connected to a set of gears 108 through a section of waveguide 105. Motor 106 is mechanically linked to antenna 104 through gears 108 and causes antenna 104 to rotate at a substantially constant and predetermined rate. Antenna resolver 112 is also linked through its input rotary shaft to gears 108 and antenna 104. Its input shaft is rotated preferably at the same rate as antenna 104.

Signals going to and coming from antenna 104 are coupled through rotary joint 110 within antenna unit 101 through wave-guide section 115 to duplexer 114. Receive signals are passed through duplexer 114 to passive limiter 116 to the input of receiver 120. Duplexer 114 isolates the transmit pulses produced by transmitter-modulator 118 from receiver 120 and couples the receive signals directly from waveguide 115 to the input of receiver 120 without substantial loss. Passive limiter 116 provides an absolute amplitude limit upon input signals to protect the input circuitry of receiver 120 from being overloaded from signals picked up from nearby radar transmitters.

Transmitter-modulator 118 produces radar pulses in response to an input trigger signal from timing generator 144 within indicator unit 140. The PRF (pulse repetition frequency) of the transmitted radar pulses is entirely determined by the repetition rate of the MTR trigger signal produced by timing generator 144. In previous radar systems in which the PRF was a function of the radar range setting, a plurality of signals indicative of the various possible range settings was coupled to the transmitter-modulator. A decoding circuit then determined the appropriate PRF for the range chosen. With the present system however, only a single trigger signal need be provided.

The width of pulses transmitted may also be a function of the radar range scale setting. It may, for example, be desirable to use a narrower pulse on shorter range scales in order to obtain a greater definition than would be possible using the longer pulses necessary to achieve an acceptable signal-to-noise ratio on the longer ranges. However, it has been found not necessary to provide a different pulse width for every possible range setting value. For example, in the preferred system embodiment of the invention there are 10 different range settings between 0.25 and 64 nautical miles. It has been found that only three different pulse widths of approxmately 60, 500, and 1000 nanoseconds are practically required. Only a two bit digital signal then need be coupled between timing generator 144 and transmitter-modulator 118 to select among the three pulse widths. As there are many fewer pulse widths required than are range scale values selectable, many fewer lines or signals need be passed between timing generator 144 and transmitter-modulator 118 than were needed in previous systems.

In previous systems a trigger pulse was generated within the MTR unit which was coupled to both the modulator and display circuitry. Because of certain characteristics of the most commonly employed modulators, the delay time between application of a trigger pulse and generation of the actual transmitted pulse may vary. This is especially true between ranges. Because of this unpredictable delay difference targets in previously known radar systems would sometimes be displayed having an inaccurate jagged edge caused by the sweep starting either too early or too late. With the system constructed in accordance with the present invention, this problem has been eliminated.

Transmitter-modulator 118 produces an MTR ACKNOWLEDGE pulse at the commencement of each transmit pulse. This MTR ACKNOWLEDGE pulse coupled to timing generator 144 marks the beginning of the start of the radar sweep for each of the video signal processing circuits within indicator unit 140. Because the MTR ACKNOWLEDGE pulse is precisely aligned with the commencement of each radar pulse registration between adjacent sweep lines upon the display screen is maintained to a high precision. Thus, the actual shapes of targets are accurately presented with no jagged edges caused by imprecise synchronization of the start of the display sweep with the actual transmitted pulse.

Transmitter-modulator 118 also produces a sensitivity time control (STC) signal to control the gain within receiver 120. As is well-known in the art, the STC signal is used to vary the gain of receiver 120 during each radar pulse period. For signals received from targets nearby the gain is reduced. In this manner the amplifying circuitry within receiver 120 is prevented from being overloaded by the strong signals from nearby targets and locally caused interference and a display having a substantially constant brilliance is produced.

The analog video signal produced at the output of receiver 120 is converted to a serial stream of digital data by analog/digital converter 148 within indicator unit 140. The rate at which samples are taken of the analog video signal for digitization and the length of the time period from the start of the radar pulse during which the analog video signal is digitized is dependent upon the radar range scale setting. For the shorter ranges, a higher sampling rate and shorter time period are used.

The digitized video signal is read into digital video data storage memory 150 under control of clock pulses from timing generator 144. Digital video data storage memory 150 stores the digitized video signal from an entire radar pulse time period. The range to which the signal is stored is of course dependent of the range scale setting. The digital video signal is read out of digital video data storage memory 150 for display upon cathode-ray tube 172 in a second time period also determined by the rate of clock pulses coming from timing generator 144. The second time period may be greater than or less than or the same as the first time period during which the video signal was read into digital video data storage memory 150. Read out occurs preferably immediately following the first time period and before commencement of the next succeeding radar time period. In preferred embodiments, the second time period is substantially constant and independent of the first time period. In this manner, with the constant readout time period the writing or deflection rate of the beam of cathode-ray tube 172 is also constant so that the display produced is of constant intensity independent of the radar range scale setting. For short ranges, the second time period during which the digital signals are read out from digital video data storage memory 150 and displayed is substantially greater than the time period during which the signals were read in. Because of the increase in time period, the writing rate of the beam of the cathode ray tube 172 is decreased over that which would be required should the video signal be displayed at the same rate at which it is received. Hence, the brightness of the display upon short ranges is greatly increased over that of previously known systems. The preferred manner of video signal digitization, storage, and read out is described in United States patent application Ser. No. 612,882, now abandoned, filed Sept. 12, 1975 which is a continuation of application Ser. No. 413,130, filed Nov. 5, 1973 (now abandoned), and assigned to the present assignee, the specification of which is herein incorporated by reference.

Interference rejection circuit 152 is provided to nullify the interference effects caused by nearby radar transmitters operating within the same frequency band. This type of interference, caused by reception of the transmitted pulses from the nearby radar, appears as plural spiral arms radiating outward from the center of the radar presentation. Interference rejection circuit 152 operates to substantially cancel this type of interference from the radar presentation without substantially effecting the presentation of desired targets. A switch is located upon control panel 146 which permits the operator to turn interference rejection circuit 152 ON and OFF as desired. The details of the construction of interference rejection circuit 152 are contained in copending application Ser. No. 714,171, filed Aug. 13, 1976, assigned to the present assignee, the specification of which is herein incorporated by reference. The final video output signal produced at the output of interference rejection circuit 152 is coupled to video amplifier 166 via video signal summer 160.

Also provided is variable range marker circuit 154. Variable range marker circuit 154 produces an output video signal in the form of a short pulse for each radar pulse to display a circular range ring mark at a distance from the center of the radar display determined by the setting of range marker adjustment 156. Range marker adjustment 156 may physically be a part of control panel 146. A display device 158 provides a digital read out to the operator of the distance from the radar antenna to the target upon which the variable range mark is positioned. The output variable range mark video signal from variable range mark circuit 154 is coupled to video amplifier 166 through video signal summer 160.

Timing generator 144 furnishes clock and other timing signals used for the various circuits within indicator unit 140. An internal oscillator within timing generator 144 produces the clock pulses at predetermined periods. The heading flash from antenna resolver 112 which is produced each time the antenna beam passes the forward direction of the ship is reclocked by the clock pulses produced by the oscillator within timing generator 144 and coupled as a video pulse through video signal summer 160 to video amplifier 166 to produce a mark on the screen to indicate to the operator when the antenna beam so passes the bow of the ship. Timing generator 144 also produces the MTR TRIGGER signal as a pulse at predetermined fixed intervals depending upon the radar range scale setting as relayed from control panel 146. The MTR ACKNOWLEDGE signal from transmitter-modulator 118 is used by timing generator 144 to produce a SWEEP GATE signal which is a logic signal which assumes the high or active state in the time period during which video signals are being received. The SWEEP GATE signal is set in the active state as soon as the MTR ACKNOWLEDGE signal is received and set to the low or inactive state at the end of the time period depending upon the range setting selected.

Upon control panel 146 are mounted the various operator actuable controls for adjusting and determining the operation of the various circuits within the radar system. A range control is provided that determines the maximum range at which targets are to be displayed. This distance corresponds to the distance at the edge of the cathode ray tube screen. ON/OFF switches are provided for operating MTR power module 122, motor 106 of antenna 101 via MTR power module 122, interference rejection circuit 152, variable range marker circuit 154, and indicator power module 174. A switch is provided to select between head up (the direction in which the ship is pointing) or north up at the top of the display presentation.

For generating displays in which north rather than the current ship's heading is represented at the top of the display screen, north stabilization circuit 142 modifies the signals received from antenna resolver 112 before coupling them to display position resolver 162. Otherwise, for displays in which the ship's heading is displayed at the top of the screen, the signals from antenna resolver 112 are coupled directly to display position resolver 162. Display position resolver 162 takes the output signals from either antenna resolver 112 or north stabilization circuit 142 in the form of modulated sine and cosine waveforms and produces therefrom DC voltages for each radar sweep representing X and Y sweep increments. Sweep waveform generator 164 produces X and Y ramp waveforms, the maximum amplitudes of which are determined by the DC voltages from display position resolver 162. Generation of the two ramp waveforms commences at the time marked by the beginning of the DELAYED SWEEP GATE signal from interference rejection circuit 152 which in turn was produced by delaying the SWEEP GATE signal from timing generator 144 by one or more clock periods to permit interference rejection circuit 152 to perform its operation. The X and Y ramp waveforms are each coupled to X and Y deflection amplifiers 168 where they are amplified and coupled to X and Y deflection coils 170 for deflecting the beam of cathode ray tube 172 in the manner well-known in the art. The output of video amplifier 166 is coupled to cathode 176 of cathode ray tube 172 for modulating the beam intensity thereof.

The high voltage applied to the accelerating anode of cathode-ray tube 172 and all other operating voltages for the various circuits within indicator unit 140 including the voltages for biasing and operating all the logic circuits contained therein are provided by indicator power module 174. Indicator power module 174 is, as is MTR power module 122 preferably a switching power supply capable of producing at its output a plurality of voltages having the required current furnishing capabilities. The switching frequency of indicator power module 174 and that of MTR power module 122 are selected intermediate the PRF rate as determined by timing generator 144 in accordance with the range setting and the rate of digitization of the analog video signal by analog/digital converter 148. By operating the power modules at a switching rate intermediate the PRF and digitization rates, interference effects are eliminated.

Figure 3:
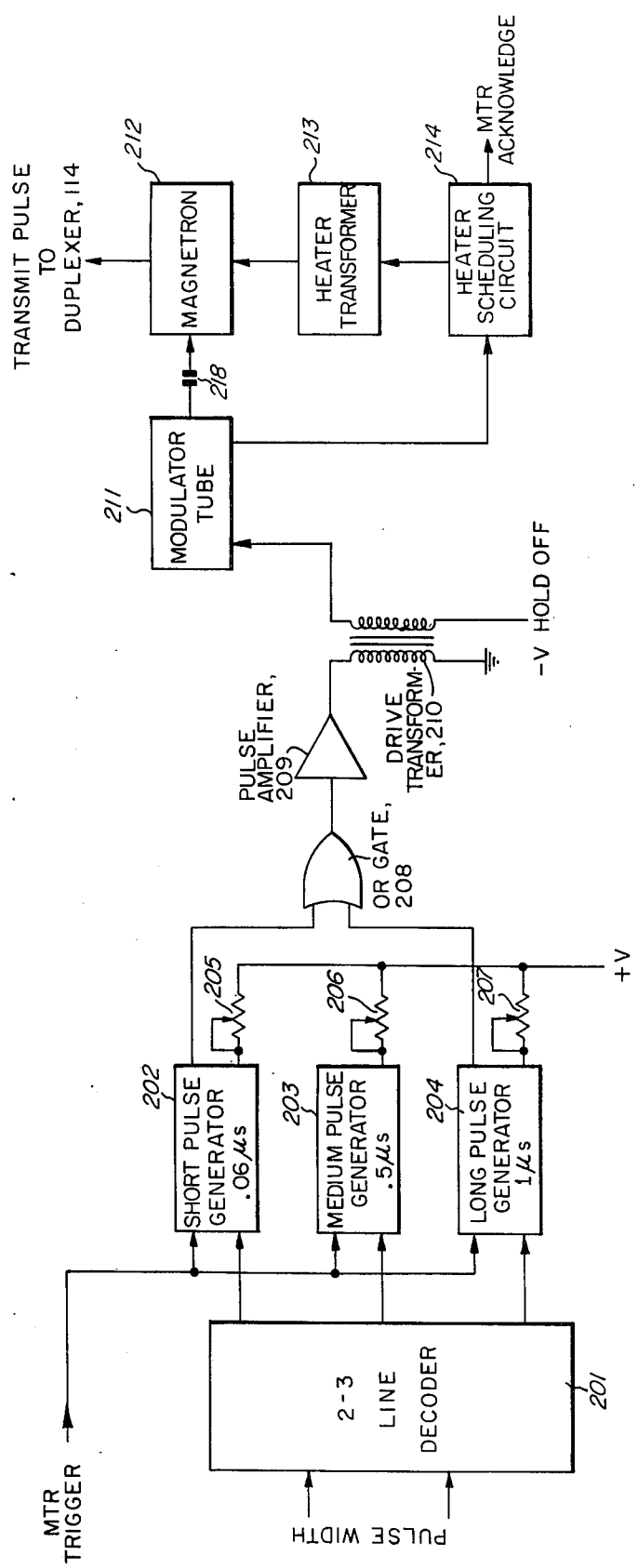
FIG. 3 is a block schematic diagram of a portion of the transmitter-modulator shown in FIG. 2.

Referring next to FIG. 3 there is shown a block/schematic diagram of that portion of transmitter-modulator 118 used for producing the output radar pulses which may be of varying pulse widths and repetition rates. The PULSE WIDTH signal from control panel 146 is received as a two bit digital code where, for example, 00 represents the shortest pulse width, 01 represents a medium pulse width, and 10 represents the longest of three pulse widths. This digital PULSE WIDTH signal is coupled to 2-3 line decoder 201 which activates one of three output lines depending upon the binary status of the input PULSE WIDTH signal. The upper output line from 2-3 line decoder 201 is activated for the shortest pulses, the middle line for the medium length pulses, and the lower line for the longest pulses.

It is generally desirable to vary the pulse width depending upon the range selected. Shorter pulses are preferred for shorter ranges for a high resolution while longer pulses are preferred on longer ranges for high sensitivity. In the preferred embodiment, pulse widths of 0.06 microseconds, 0.5 microseconds, and 1.0 microseconds are employed although others may be used as well. Pulse generators 202-204, monostable multivibrators having provisions for external pulse width control, produce pulses of appropriate width upon activation of both input lines. The one of pulse generators 202-204 selected is of course determined by the status of the output lines from 1-3 line decoder 201. A pulse is produced by the selected generator each time an MTR TRIGGER pulse signal is received from timing generator 144 of indicator unit 140. Potentiometers 205-207 are adjusted to give the proper pulse width from each pulse generator 202-204. The three output lines from the three pulse generators 202-204 are merged through OR gate 208 to a single signal line. Hence, on the output line from OR gate 208 there appears a series of pulses of the selected width at the pulse repetition rate determined by the rate MTR TRIGGER signal applied from timing generator 144. Also, depending upon the range selected, the aforementioned sensitivity time control signal coupled from the transmitter modulator 118 to receiver 120 of FIG. 2 reduces the gain of the receiver during each radar pulse by reducing the gain of the amplifying circuitry in the receiver in a well-known manner to prevent overloading by strong signals from nearby targets and local interference to provide a display having substantially constant brilliance.

The output signal from OR gate 208 is amplified from its logic level by pulse amplifier 209 to a voltage and impedance level sufficient for driving the primary of drive transformer 210. One end of the secondary winding of drive transformer 210 is returned to a negative voltage -V HOLD OFF sufficient to hold modulator tube 211 below cutoff in the absence of an applied pulse. When a pulse is produced to the output of OR gate 208, drive transformer 210 provides sufficient STEP-UP between the output of pulse amplifier 209 and the control grid of modulator 211 to raise the voltage of the control grid above -V HOLD OFF and to hence drive modulator tube 211 towards saturation. The output produced on the plate of modulator tube 211 is coupled through capacitor 218 to the cathode of magnetron 212. Magnetron 212 produces an output pulse to duplexer 114 each time a pulse is received from modulator tube 211.

Power for the heater of magnetron 212 is provided by heater scheduling circuit 214 through heater transformer 213. Heater scheduling circuit 214 provides proportional heater voltage control in accordance with the average anode input power to magnetron 212. The average anode input power is in turn equivalent to the magnetron ON-OFF duty cycle which is affected by both the pulse repetition frequency and pulse width input. Duty cycle sensing for producing control of the magnetron heater power is done from the cathode circuit of modulator tube 211. Generally, if the ON duty cycle time of modulator tube 211 exceeds a preset level, heater scheduling circuit 214 decreases the heater voltage and hence power. If the average anode power decreases below the preset level, as may occur due to magnetron aging, heater scheduling circuit 214 accordingly increases the magnetron heater voltage. Also, because of the reactance-limited design of heater transformer 213, the magnetron's peak cold in rush surge current is limited to a safe short-circuit value for circuit START-UP.

Referring now to FIG. 4 there is shown a schematic diagram of heater scheduling circuit 214. The magnitude of the current through modulator tube 211 during the pulse ON times is sensed across low resistance resistor 340 in series with the cathode of modulator tube 211. The signal produced across resistor 340 is coupled to the floating common point of heater scheduling circuit 214 through saturable reactor 310 and diode 307 to charge capacitor 306 during the pulse ON times. Saturable reactor 310 prevents short pulses from charging capacitor 306 to maintain maximum heater power for such short pulses. The peak voltage produced across capacitor 306 is otherwise in proportion to the amplitude of the modulator tube peak current.

During the interpulse period when modulator tube 211 is not conducting, capacitor 309 is charged through resistor 308 from the voltage which had previously been stored across capacitor 306 during the pulse ON time. A portion of the voltage across capacitor 309 determined by the setting of potentiometer 314 is coupled to the base of transistor 317. Transistor 317 is the input of a very high impedance D'arlington circuit including transistors 317-319. A substantially linear relationship exists between the voltage at the base of transistor 317 and the magnetron heater voltage with a neagative slope relationship. Thus, since the voltage applied to the base of transistor 317 is in proportion to the ON duty cycle, as the duty cycle increases the voltage applied to the heater of magnetron 212 decreases. In a preferred embodiment, a nominal 6.3 volt heater voltage is applied to the magnetron tube heater during quiescent operation and for short pulses. When pulses of the maximum length are used, heater voltage decreases to a value determined by the setting of potentiometer 314. For long pulses, it may be desired even to reduce the heater voltage to zero or near zero voltages because sufficient self-heating occurs due to anode pulsing. However, it is to be noted that with the invention, even at very low heater voltages, variations in output power will be automatically compensated for by the circuit.

The D'arlington circuit including transistors 317-319 buffers the voltage applied to the base of transistor 317 to a lower impedance level as seen across capacitor 321. The output voltage on the emitter of transistor 319 determines the peak of the square wave driving signals applied to the primary of transformer 213 through a free-running multivibrator including transistors 329 and 338 as the active switching elements thereof. Transistors 329 and 338 are turned on and conduct alternately in a 50% duty cycle. The frequency of oscillation of the multivibrator is determined by the inductance of the primary windings of transformer 213, the values of capacitors 322 and 325, and the values of resistors 323 and 324. In the preferred embodiment with the components specified in the Parts List of Appendix I, an oscillation frequency of approximately 40 KHz is achieved for a typical magnetron tube load with a tube capable of producing a peak output of approximately 20 KW.

Protection of transformer 213 and the circuitry connected thereto against short-circuit currents caused by magnetron heater shorting may be achieved by using for transformer 213 a transformer for which the inductive and other losses increase rapidly above the normal operating frequency of the multivibrator. When the magnetron heater shorts out or becomes a very low impedance, the impedance change is reflected back into the primary of transformer 213 lowering the effective inductance of the primary windings thereof and increasing the frequency of operation of the multivibrator. With the component value specified in Appendix I, the operating frequency will increase from approximately 40 KHz to approximately 80 KHz for a shorted magnetron heater. With the losses caused by transformer 213 operated at the higher frequency, very little power will be transferred into the shorted magnetron heater circuit or reflected back into the multivibrator circuit.

Heater scheduling circuit 214 also produces the ACKNOWLEDGE pulse signal is used for synchronization of timing generator 144 and other operations of indicator unit 140. The voltage produced across sensing resistor 340 is coupled through resistor 302 to the cathode of Zener diode 301, the anode of which is coupled to chassis ground, the same ground reference point used by indicator unit 140. The ACKNOWLEDGE pulse is thus produced coindicent with the application of operating power to the output magnetron tube and hence with a fixed time relationship with the production of the radar pulses and the time of their actual emission. Zener diode 301 reduces the amplitude of the voltage produced across sensing resistor 340 to a predetermined preferred value, here 14 V.

Although preferred embodiments of the invention have been described, it is believed that numerous modifications and alterations thereto would be apparent to one having ordinary skill in the art without departing from the spirit and the scope of the invention.

APPENDIX

Parts List for Figure 4

Resistors

| | | | |
|---|---|---|---|
| 302 | 27Ω | 316 | 50KΩ |
| 303 | 680Ω | 323, 324 | 100Ω, 1W |
| 308, 327, 340 | 470Ω | 320 | 1KΩ |
| 312 | 22Ω | 326 | 2.2KΩ |
| 314 | 50KΩ | 334 | 680Ω, 2W |

Capacitors

| | | | |
|---|---|---|---|
| 306, 321, 335 | 10µf., 75V. | 322, 325 | 0.047µf, 600V. |
| 309 | 1µf., 100V. | 333 | 0.1µf, 600V. |

Transistors

| | | | |
|---|---|---|---|
| 317 | 2N2222A | 319 | General Electric D45H2 |
| 318 | 2N2907A | 329, 338 | 2N3019 |

Diodes

| | |
|---|---|
| 301 | Zener 14V, 5W |
| 307, 315, 328, 331, 332, 336, 337, 339 | Raytheon 587306-2 |

Inductor

| | |
|---|---|
| 310 | Raytheon 168003-1 |

Transformer

APPENDIX-continued

Parts List for Figure 4
213  Raytheon 167050-1

All resistors ¼ watt, 5% unless otherwise specified.

What is claimed is:

1. A radar system comprising in combination:
timing generator means for initiating production of radar pulses;
means for transmitting said radar pulses in response to said initiating means;
means for producing an acknowledge signal having a fixed time relationship to said transmitted radar pulses;
means for receiving returned radar signals; and
means for producing a visual display responsive to the received returned radar signals;
said timing generator means initiating a sweep gate signal for synchronizing the start of the visual sweep of said display in response to said acknowledge signal, whereby the acknowledge signal has a fixed time relationship with the commencement of each of said transmitted radar pulses to prevent jitter between the start of the visual sweep and returns of said radar pulses.

2. A radar system comprising in combination:
timing generator means for initiating production of radar pulses;
means for transmitting said radar pulses in response to said initiating means;
means for producing an acknowledge signal having a fixed time relationship to said transmitted radar pulses;
means for receiving returned radar signals and producing video representations of said signals;
means for producing a visual display responsive to the received returned radar signals;
said timing generator means initiating a sweep gate signal for synchronizing the start of the visual sweep of said display in response to said acknowledge signal, whereby the acknowledge signal has a fixed time relationship with the commencement of each of said transmitted radar pulses to prevent jitter between the start of the visual sweep and returns of said radar pulses;
means for storing said digital video representations at least for some of said representations;
analog to digital converter means coupled to said generator means for writing said digital video representations from said receiver means into said storing means at a first rate, and
said storing means being adapted in response to said timing generator means for reading out said digital video representations at a 3. A radar system comprising in combination:
trigger means for initiating production of transmitted radar pulses;
means for transmitting said pulses;
means for producing an acknowledge signal having a fixed time relationship to said transmitted radar pulses and directly produced by said transmitted radar pulses;
means for receiving returned radar signals;
means for producing a display in response to the received return radar signals; and
wherein said means for producing an acknowledge signal having a fixed time relationship to said transmitted radar pulses comprises:
means for sensing one or more signals of said initiating means.

4. A radar system comprising in combination:
trigger means for initiating production of transmitted radar pulses;
means for transmitting said pulses;
means for producing an acknowledge signal having a fixed time relationship to said transmitted radar pulses and directly produced by said transmitted radar pulses;
means for receiving returned radar signals;
means for producing a display in response to the received return radar signals; and
wherein said means for producing an acknowledge signal having a fixed time relationship to said transmitted radar pulses comprises:
means for sensing one or more signals of said initiating means, said initiating means comprising:
a modulator tube.

5. A radar system comprising in combination:
trigger means for initiating production of transmitted radar pulses;
means for transmitting said pulses;
means for producing an acknowledge signal having a fixed time relationship to said transmitted radar pulses and directly produced by said transmitted radar pulses;
means for receiving returned radar signals;
means for producing a display in response to the received return radar signals; and
wherein said means for producing an acknowledge signal having a fixed time relationship to said transmitted radar pulses comprises:
means for sensing one or more signals of said initiating means, wherein said initiating means comprises:
a modulator tube, and
said sensing means comprises:
means for sensing cathode current in said tube.

6. A radar system comprising in combination:
trigger means for initiating production of transmitted radar pulses;
means for transmitting said pulses;
means for producing an acknowledge signal having a fixed time relationship to said transmitted radar pulses and directly produced by said transmitted radar pulses;
means for receiving returned radar signals;
means for producing a display in response to the received return radar signals; and
wherein said means for producing an acknowledge signal having a fixed time relationship to said transmitted radar pulses comprises:
means for sensing one or more signals of said initiating means, said initiating means comprising: a solid-state modulator.

7. A radar system comprising in combination:
trigger means for initiating production of transmitted radar pulses;
means for transmitting said pulses;

means for producing an acknowledge signal having a fixed time relationship to said transmitted radar pulses and directly produced by said transmitted radar pulses;

means for receiving returned radar signals;

means for producing a display in response to the received return radar signals; and wherein said means for producing an acknowledge signal having a fixed time relationship to said transmitted radar pulses comprises:

means for sensing one or more signals of said initiating means, said transmitting means comprising:

a magnetron tube.

8. The combination of claim 3 further comprising pulse width generator means connected to said initiating means and including variable resistive means for varying the width of said pulses.

* * * * *

UNITED STATES PATENT OFFICE
CERTIFICATE OF CORRECTION

Patent No. 4,058,810      Dated Nov. 15, 1977

Inventor(s) Joseph E. Bryden

It is certified that error appears in the above-identified patent and that said Letters Patent are hereby corrected as shown below:

Column 8, line 11: change "1" to - 2 - ;

Column 9, line 28: change "neagative" to - negative - ;

Column 10, in the appendex under transistors change:

"General Electric D 45 H2" to - General Electric D 45 112 -

Column 11, line 57: after "a" add - second rate - .

Signed and Sealed this

Fifteenth Day of August 1978

[SEAL]

Attest:

RUTH C. MASON
Attesting Officer

DONALD W. BANNER
Commissioner of Patents and Trademarks